(12) United States Patent
Leung et al.

(10) Patent No.: US 11,536,395 B2
(45) Date of Patent: Dec. 27, 2022

(54) CABLE SUPPORT CLIP FOR MEDICAL DEVICE WORKSTATION

(71) Applicant: Verathon Inc., Bothell, WA (US)

(72) Inventors: Hugh Leung, Burnaby (CA); Karen Langman, Kirkland, WA (US); Daniel Roodnick, Delta (CA)

(73) Assignee: VERATHON INC., Bothell, WA (US)

( * ) Notice: Subject to any disclaimer, the term of this patent is extended or adjusted under 35 U.S.C. 154(b) by 264 days.

(21) Appl. No.: 16/792,597

(22) Filed: Feb. 17, 2020

(65) Prior Publication Data

US 2021/0254756 A1 Aug. 19, 2021

(51) Int. Cl.
*F16L 3/22* (2006.01)
*F16L 3/06* (2006.01)
*A61B 90/00* (2016.01)
*A61B 50/13* (2016.01)

(52) U.S. Cl.
CPC ............... *F16L 3/06* (2013.01); *A61B 50/13* (2016.02); *A61B 90/37* (2016.02)

(58) Field of Classification Search
CPC .... F16L 3/06; F16L 3/13; A61B 50/13; A61B 90/37; H02G 3/32
USPC ................ 248/68.1, 316.7; 24/455; 174/68.1
See application file for complete search history.

(56) References Cited

U.S. PATENT DOCUMENTS

| | | | | |
|---|---|---|---|---|
| 2,542,442 | A * | 2/1951 | Weber | F16L 3/223 29/451 |
| 7,500,644 | B2 * | 3/2009 | Naudet | H02G 3/32 248/65 |
| 9,534,708 | B2 * | 1/2017 | Cripps, II | F16L 3/221 |
| 2007/0246613 | A1 * | 10/2007 | Kennedy | H02G 3/32 248/56 |
| 2008/0086086 | A1 * | 4/2008 | Field | G16H 20/17 700/282 |
| 2014/0233026 | A1 * | 8/2014 | Barrett | G01N 21/05 356/246 |
| 2018/0135779 | A1 * | 5/2018 | Bartos | F16L 3/221 |
| 2018/0306351 | A1 * | 10/2018 | Leo, Sr. | F16L 3/13 |
| 2021/0247002 | A1 * | 8/2021 | Dallmann | H02G 3/32 |
| 2021/0324972 | A1 * | 10/2021 | Arnold | F16L 3/243 |

FOREIGN PATENT DOCUMENTS

| | | | | |
|---|---|---|---|---|
| CA | 2437286 C | * | 4/2008 | ............ A61B 19/22 |
| DE | 19840136 A1 | * | 3/2000 | ............ F16L 3/1075 |

* cited by examiner

*Primary Examiner* — Todd M Epps
(74) *Attorney, Agent, or Firm* — Snyder, Clark, Lesch & Chung, LLP

(57) ABSTRACT

A cable clip for use with a medical instrument system comprises a base member; a first prong projecting from the base member; and a second prong projecting from the base member. The first prong and the second prong project in a spaced, parallel manner relative to each other and the first prong is offset from the second prong in at least two dimensions.

18 Claims, 3 Drawing Sheets

CABLE SUPPORT CLIP FOR MEDICAL DEVICE WORKSTATION

BACKGROUND

The present invention relates to the field of medicine, and more specifically to mounting of devices used in performing medical procedures.

Medical professionals often need to position instruments, such as cameras, position trackers, patient monitors, display screens, laptop computers, etc. and their associated accessories within a relatively short distance from the patient treatment region (e.g., a surgical field) at a height similar or higher than that of the patient. Keeping such devices and accessories organized is paramount in providing a safe and efficient operating field.

DETAILED DESCRIPTION OF THE PREFERRED EMBODIMENTS

The following detailed description refers to the accompanying drawings. The same reference numbers in different drawings may identify the same or similar elements. Also, the following detailed description does not limit the invention.

A multi-cable support and organization clip for use with a video display medical instrument system is described herein. As shown and described below, a video display medical instrument system, such as a video intubation instrument (e.g., a laryngoscope) or other video endoscope system may include a display monitor mounted to a surgical cart or workstation. A multi-cable clip may be attached to one of the display monitor or a display mount for retaining connector ends of a plurality of device video cables at discrete positions relative to the display monitor. During use, an operator may identify and retrieve a suitable video cable based on its position within the clip. Similarly, when the procedure is complete, or use of a particular video instrument is complete, the respective video cable may be returned to its defined position within the clip.

Figure 1:
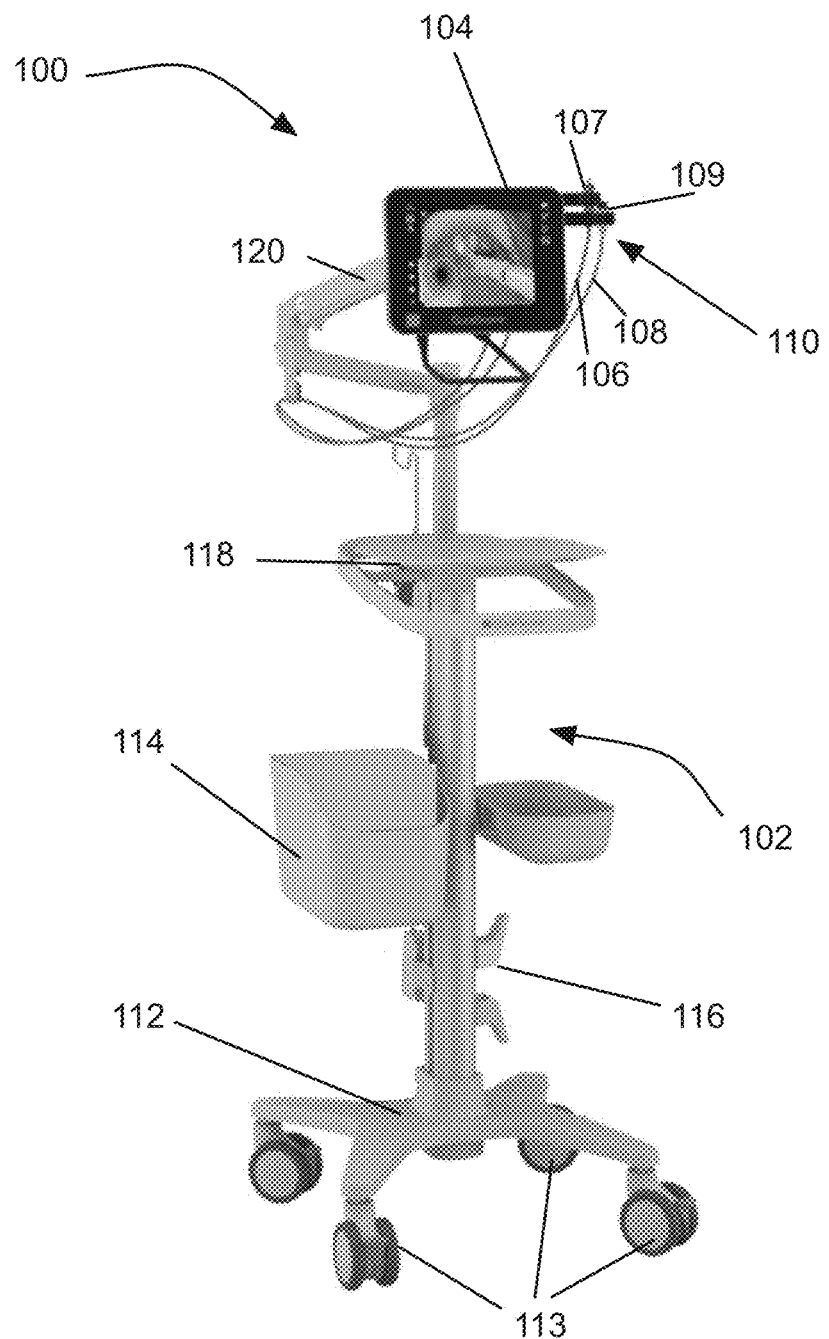
FIG. 1 is a diagram illustrating a laryngoscope system consistent with embodiments described herein.

FIG. 1 illustrates a video display medical instrument system 100 consistent with implementations described herein. As shown, video display medical instrument system 100 includes a workstation 102, a display monitor 104, first video cable 106, second video cable 108, and cable clip 110. In some implementations, such as that shown in FIG. 1, workstation 102 may include a base 112 to which a plurality of wheels 113 are affixed, as well as a plurality of bins 114, hooks 116, and/or trays 118 in addition to a display monitor mount 120 configured to allow display monitor 104 to be secured to workstation 102. In some implementations, display monitor mount 120 includes an articulated arm that allows display monitor 104 to be positioned independently of a positional orientation of workstation 102.

Consistent with implementations described herein, cable clip 110 may be secured to display monitor 104 or display monitor mount 120 such that cable clip 110 projects outwardly from (e.g., toward a side of) display monitor 104. In some implementations, the location of cable clip 110 relative to display monitor 104 may be proximal to a location of video inputs on display monitor 104, although this is not required.

FIGS. 2A, 2B, 2C, and 2D are front, front isometric, top, and top isometric views, respectively, of an exemplary cable clip 110 configured in a manner consistent with embodiments described herein. As shown in FIGS. 2A-2D, cable clip 110 may include a base member 200 and an overmold portion 205. Base member 200 may be formed of a rigid material, such as aluminum, stainless steel, or a rigid plastic. As shown, base member 200 includes an attachment portion 210, a fork portion 215, a first prong base portion 220, and a second prong base portion 225. In some embodiments the portions of base member 200 may be formed from a single, unitary material; however, in other implementations, the portions of base member 200 described herein may be independently fabricated and secured together in any appropriate manner (e.g., screws, adhesives, clips, etc.).

Consistent with implementations described herein, attachment portion 210 may have a generally planar, bar-like configuration with a length sufficient to distance fork portion 215 from an attachment point on display monitor 104 or display monitor mount 120 to avoid interference between display monitor 104 and cables supported in clip 110 during use. In some embodiments, cable clips having attachment portions 210 of different lengths may associated with different size display monitors.

Fork portion 215 may include a transition area between attachment portion 210 and first/second prong base portions 220/225. Consistent with embodiments described herein, prong base portions 220/225 project outwardly from fork portion 215 in a spaced, parallel manner and are offset from each other in both the y and z dimensions, as shown most clearly in FIG. 2B. Such offsets may be configured to provide for easy visual and tactile distinction between the cables supported thereby. For example, for a cable clip having an overall length of between 8 and 10 inches from the tip of overmold portion 205 to a base of attachment portion 210, first prong portion 220 may be offset from second prong portion 225 by approximately 1.75-2.0 inches in the y-direction (i.e., front to back), and approximately 0.75-1.25 inches in the z-direction (i.e., top to bottom).

Although not shown in the figures, to facilitate secure adhesion of overmold portion 205 to base member 200, one or more of attachment portion 210 and/or first and second prong base portions 220/225 may include one or more through holes formed there, through which overmold material may flow during manufacture, thereby permanently securing overmold portion 205 to base member 200.

Overmold portion 205 forms an outer surface of cable clip 110 and is formed from a resilient or semi-rigid material, such as a polymer or rubber. During manufacture of cable clip 110, base member 200 may be secured within a mold that defines the outer configuration of overmold portion 205, such that the thickness of overmold portion 205 is substantially uniform throughout. An overmold material, such as a polymer material may be formed, such as via injection molding or like, to fill the mold between the confines of the mold and base member 200.

Figure 2A:
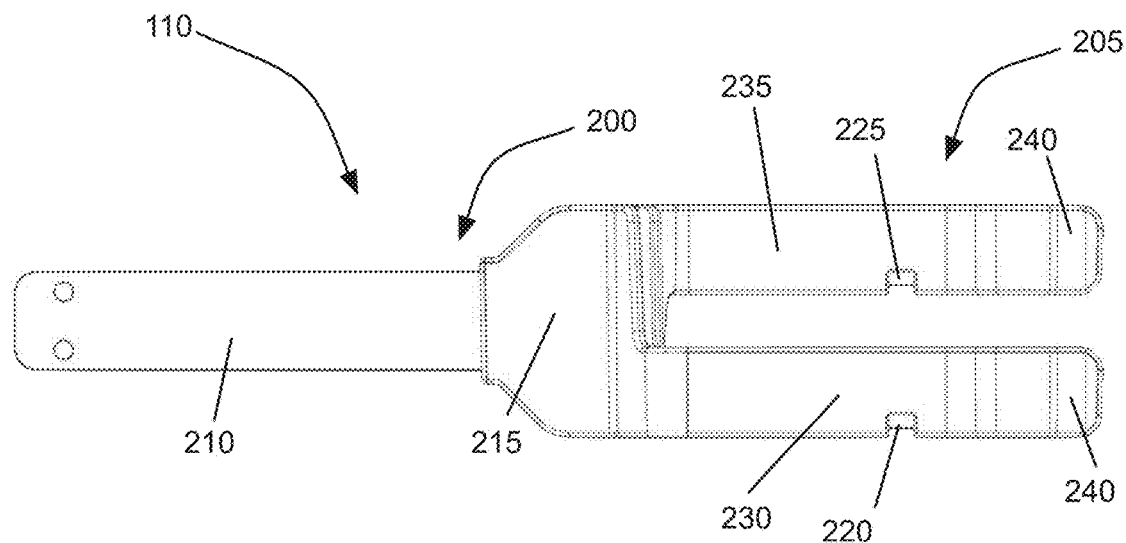
FIG. 2A is front view of an exemplary cable clip configured in a manner consistent with embodiments described herein.
Figure 2B:
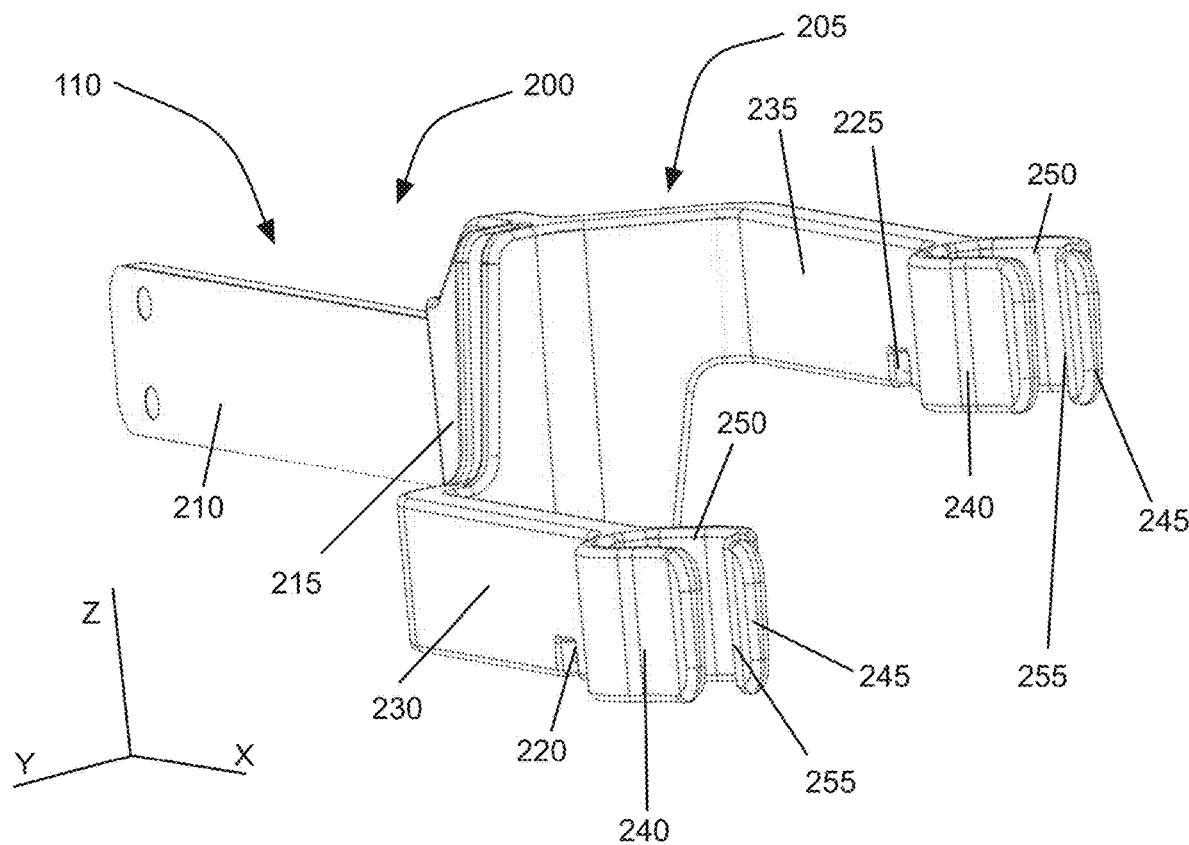
FIG. 2B is a front isometric view of an exemplary cable clip configured in a manner consistent with embodiments described herein.
Figure 2C:
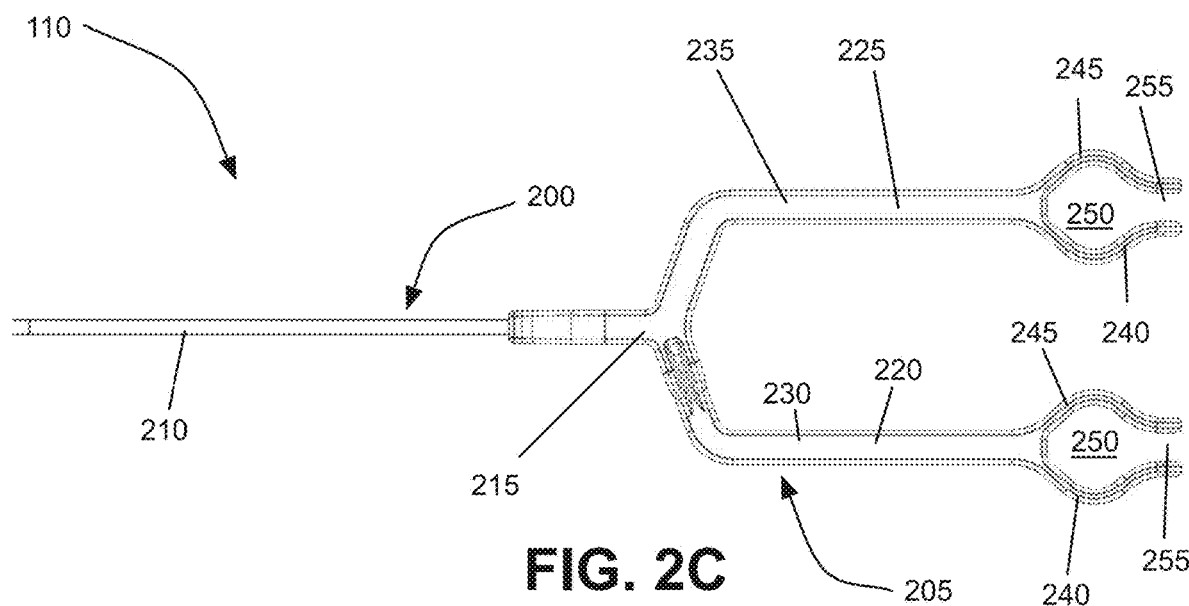
FIG. 2C is a top view of an exemplary cable clip configured in a manner consistent with embodiments described herein.
Figure 2D:
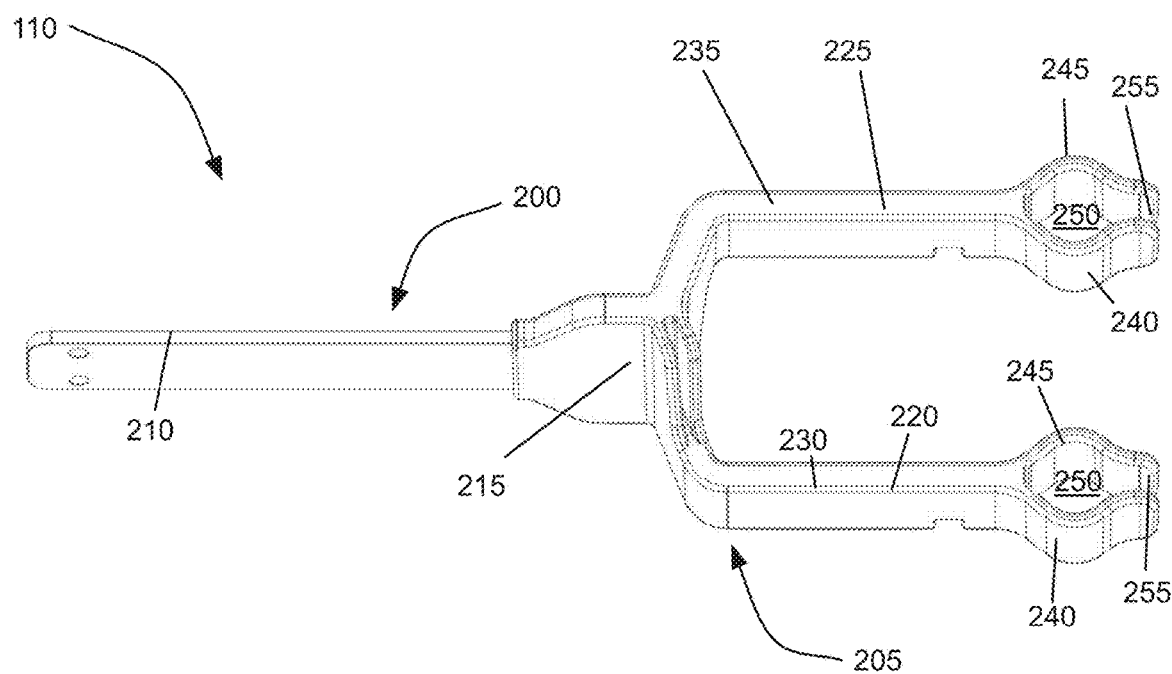
FIG. 2D is a top isometric view of an exemplary cable clip configured in a manner consistent with embodiments described herein.

As shown in FIGS. 2A-2D, overmold portion 205 may cover at least fork portion 215 and first and second prong base portions 220/225 of base member 200. Furthermore, consistent with embodiments described herein, overmold portion 205 may include first and second cable grasping portions 230/235. As shown in FIG. 2C, grasping portions 230/235 may extend beyond first and second prong base portions 220/225. Each grasping portion 230/235 includes opposing finger portions 240/245 that define an opening on which a cable end, e.g., a terminal, or interface plug, may be supported. In one implementation, finger portions 240/245 may each including an opposing arcuate configuration that defines a cable support opening 250 for receiving and supporting a generally tubular cable interface plug therein. An open portion 255 defined by the terminal tips of finger portions 240/245 is configured to allow cables to pass therethrough to allow the cables to be introduced to and removed from cable clip 110. In other implementations, a configuration of finger portions 245 may be other than arcuate, such as rectangular, etc. based on a configuration of a cable terminal to be secured therein.

As shown in FIG. 1, terminals 107 and 109 of cables 106 and 108 may be secured within cable clip 110 in a manner consistent with embodiments described herein. By including prong and grasping portions that are offset in both the y and z directions, the location of the respective terminals 107/109 may be easily determined, even without looking. Furthermore, clip 110 provides a safe and effective storage location of cable terminals 107/109 when not in use, or during transport of workstation 102.

The foregoing description of embodiments provides illustration but is not intended to be exhaustive or to limit the embodiments to the precise form disclosed. In the preceding description, various embodiments have been described with reference to the accompanying drawings. However, various modifications and changes may be made thereto, and additional embodiments may be implemented, without departing from the broader scope of the invention as set forth in the claims that follow. For example, although injection molding is described as an exemplary method for forming grasping portions 230/235 and fingers portions 240/245, other manufacturing techniques could be used consistent with embodiments described herein, such as 3D printing, casting, blow molding, compression molding, etc. The description and drawings are accordingly to be regarded as illustrative rather than restrictive.

As set forth in this description and illustrated by the drawings, reference is made to "an exemplary embodiment," "an embodiment," "embodiments." etc., which may include a particular feature, structure or characteristic in connection with an embodiment(s). However, the use of the phrase or term "an embodiment," "embodiments." etc., in various places in the specification does not necessarily refer to all embodiments described, nor does it necessarily refer to the same embodiment, nor are separate or alternative embodiments necessarily mutually exclusive of other embodiment(s). The same applies to the term "implementation," "implementations," etc.

The terms "a," "an," and "the" are intended to be interpreted to include one or more items. Further, the phrase "based on" is intended to be interpreted as "based, at least in part, on." unless explicitly stated otherwise. The term "and/or" is intended to be interpreted to include any and all combinations of one or more of the associated items.

The word "exemplary" is used herein to mean "serving as an example." Any embodiment or implementation described as "exemplary" is not necessarily to be construed as preferred or advantageous over other embodiments or implementations.

Use of ordinal terms such as "first," "second," "third." etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

No element, act, or instruction described in the present application should be construed as critical or essential to the embodiments described herein unless explicitly described as such.

What is claimed is:

1. A cable clip, comprising:
   a base member formed of a rigid first material;
   a first prong projecting from the base member;
   a second prong projecting from the base member,
   wherein the first prong and the second prong are formed of the rigid first material;
   a first grasping portion coupled to the first prong; and
   a second grasping portion coupled to the second prong,
   wherein the first and second grasping portions are formed of a resilient second material different from the first material,
   wherein the first and second grasping portions are configured to support a terminal end of a cable therein,
   wherein the first prong and the second prong project in a spaced, parallel manner relative to each other, and
   wherein the first prong is offset from the second prong in at least two dimensions.

2. The cable clip of claim 1, wherein the first prong is offset from the second prong in a z-direction and a y-direction.

3. The cable clip of claim 2, wherein each of the first and second grasping portions comprises at least one resilient or semi-rigid finger.

4. The cable clip of claim 3, wherein the at least one finger comprises an arcuate configuration.

5. The cable clip of claim 3, wherein the at least one finger comprises a pair fingers having opposing arcuate configurations.

6. The cable clip of claim 5, wherein each of the first and second grasping portions further comprises an opening between ends of the pair of fingers for permitting a cable to pass therethrough.

7. The cable clip of claim 1, wherein the base member is adapted for mounting onto one of a display monitor, a display monitor mount, or a surgical workstation.

8. The cable clip of claim 1, further comprising an overmold portion covering at least a portion of the base member.

9. The cable clip of claim 8, wherein the base member comprises the rigid first material and the overmold portion comprises the resilient second material.

10. The cable clip of claim 9, wherein the overmold portion comprises the first and second grasping portions.

11. A surgical workstation, comprising:
a base;
a display monitor mount; and
a cable clip projecting from the display monitor mount, wherein the cable clip comprises:
  a base member formed of a rigid first material;
  a first prong projecting from the base member;
  a second prong projecting from the base member,
  wherein the first prong and the second prong are formed of the rigid first material;
  a first grasping portion coupled to the first prong; and
  a second grasping portion coupled to the second prong,
  wherein the first and second grasping portions are formed of a resilient second material different from the first material,
  wherein the first and second grasping portions are configured to support a terminal end of a cable therein,
  wherein the first prong and the second prong project in a spaced, parallel manner relative to each other; and
  wherein the first prong is offset from the second prong in at least two dimensions.

12. The surgical workstation of claim 11, further comprising a plurality of wheels secured to the base.

13. The surgical workstation of claim 11, wherein the first prong is offset from the second prong in a z-direction and a y-direction.

14. The surgical workstation of claim 11, wherein each of the first and second grasping portions comprises at least one resilient or semi-rigid finger.

15. The surgical workstation of claim 14, wherein the at least one finger comprises an arcuate configuration.

16. The surgical workstation of claim 14, wherein the at least one finger comprises a pair fingers having opposing arcuate configurations.

17. The surgical workstation of claim 16, wherein each of the first and second grasping portions further comprises an opening between ends of the pair of fingers for permitting a cable to pass therethrough.

18. The surgical workstation of claim 11,
  wherein the cable clip further comprising an overmold portion covering at least a portion of the base member,
  wherein the base member comprises the rigid first material and the overmold portion comprises the resilient second material, and
  wherein the overmold portion comprises the first and second grasping portions.

* * * * *